United States Patent
Deflorian et al.

(10) Patent No.: US 11,027,037 B2
(45) Date of Patent: Jun. 8, 2021

(54) DEVICE FOR EVAPORATING VOLATILE SUBSTANCES COMPRISING WICK AND HEAT REFLECTIVE ELEMENT

(71) Applicant: Zobele Holding SPA, Trento (IT)

(72) Inventors: Stefano Deflorian, Trento (IT); Cedric Morhain, Barcelona (ES)

(73) Assignee: Zobele Holding SPA, Trento (IT)

( * ) Notice: Subject to any disclaimer, the term of this patent is extended or adjusted under 35 U.S.C. 154(b) by 0 days.

(21) Appl. No.: 16/473,870

(22) PCT Filed: Dec. 28, 2016

(86) PCT No.: PCT/EP2016/082767
§ 371 (c)(1),
(2) Date: Jun. 26, 2019

(87) PCT Pub. No.: WO2018/121857
PCT Pub. Date: Jul. 5, 2018

(65) Prior Publication Data
US 2020/0147255 A1 May 14, 2020

(51) Int. Cl.
*A61L 9/03* (2006.01)
(52) U.S. Cl.
CPC .......... *A61L 9/037* (2013.01); *A61L 2209/111* (2013.01)
(58) Field of Classification Search
CPC ............................ A61L 9/037; A61L 2009/111
See application file for complete search history.

(56) References Cited

U.S. PATENT DOCUMENTS

| 2001/0053283 | A1 | 12/2001 | Levine | |
|---|---|---|---|---|
| 2004/0007787 | A1* | 1/2004 | Kvietok | A61L 9/048 261/26 |
| 2005/0053368 | A1 | 3/2005 | Pesu | |
| 2012/0153040 | A1 | 6/2012 | Miguens | |
| 2014/0037273 | A1 | 2/2014 | Jaworski | |

FOREIGN PATENT DOCUMENTS

EP 1372161 12/2003

OTHER PUBLICATIONS

International Search Report dated Sep. 27, 2017 from co-pending International Application No. PCT/EP2016/082767.

* cited by examiner

*Primary Examiner* — Timothy C Cleveland
(74) *Attorney, Agent, or Firm* — Don V. Kelly; Evans & Dixon, L.L.C.

(57) ABSTRACT

A device for evaporating volatile substances includes a wick (1) impregnated with volatile substances and a heating element (2) that heats the wick (1) for purposes of evaporating said volatile substances. The device further includes a reflective element (3) for reflecting the heat from the heating element (2) to said wick (1). The heating element (2) can be preferably a resistor or a ceramic heater. The reflective element (3) directs substantially all the heat provided by the heating element to the wick, thereby preventing an excessive rising of the temperature of the surface of the device.

8 Claims, 4 Drawing Sheets

DEVICE FOR EVAPORATING VOLATILE SUBSTANCES COMPRISING WICK AND HEAT REFLECTIVE ELEMENT

CROSS REFERENCE TO RELATED APPLICATION

This application is a U.S. national stage application filed under 35 U.S.C. § 371 of International Patent Application No. PCT/EP2016/082767 filed on Dec. 28, 2016. The entirety of the foregoing application is incorporated by reference herein.

STATEMENT REGARDING FEDERALLY SPONSORED RESEARCH OR DEVELOPMENT

Not applicable.

SEQUENCE LISTING, TABLE OR COMPUTER PROGRAM ON COMPACT DISC

Not applicable.

FIELD OF INVENTION

The present invention is directed to a device for evaporating volatile substances, comprising a wick impregnated with volatile substances and a heating element that heats the wick for evaporating said volatile substances.

BACKGROUND OF THE INVENTION

Electrical air fresheners have become a very common consumer product in the last decades. Most common devices are connected to the electric mains and comprise a refill containing a liquid with volatile substances and a wick that transports the liquid from the inside of the refill to the external part of the wick, where the volatile particles evaporate. This refill is placed in a device that with the help of an electrical heater promotes the evaporation of the volatile substance.

Standard technology for the heater construction typically involves either an electrical heater embedded in a ceramic casing or a nude electrical resistor placed inside a plastic housing. The ceramic casing and the plastic housing have the function to assure electrical insulation between the resistor and the surroundings.

The existing solutions for electrical devices for evaporating volatile substances have several drawbacks.

Firstly, they have generally big dimensions and each of their surfaces dissipate heat. Therefore, only part of the heat is directed towards the wick where it is needed. That leads to a lower electrical efficiency of the device.

Secondly, the heat not directed towards the wick promotes a general heating of the device that can substantially raise the temperature of the surface of the device. This is the reason why the devices have a considerable dimension, which dimension prevented the temperature at the surface exceeding a limit defined by electrical certification entities.

Therefore, the objective of the present invention is to provide a device for evaporating volatile substances that directs substantially all the heat provided by the heating element to the wick, thereby preventing an excessive rising of the temperature of the surface of the device.

SUMMARY OF THE INVENTION

With the device of the invention said drawbacks can be solved, presenting other advantages that will be described hereinafter.

The device for evaporating volatile substances according to the present invention comprises a wick impregnated with volatile substances and a heating element that heats the wick for evaporating said volatile substances. The device also comprises a reflective element for reflecting the heat from the heating element to said wick.

Thanks to this last feature, the reflective element reflects or redirects the heat radiation from the heater back towards the wick where the volatile substances are impregnated, and the heat energy that is going away from the wick is reflected back to the wick, so that a heating element which consumes less energy can be used for the same evaporation capacity.

Another advantage is that the reflected heat is not contributing to the overall heating of the external surface of the device.

Advantageously, the heating element can be a resistor or a ceramic heater, and the reflective element preferably comprises a metallic surface.

Preferably, said heating element is placed between the wick and the reflective element, and according to a possible embodiment, said heating element and/or said reflective element have a cylindrical shape and are placed one inside the other, being the reflective element external to the heating element.

If desired, said heating element and said reflective element can be joined by a base, and according to possible embodiment, said reflective element is made from two layers, a reflective layer and a base layer.

The device for evaporating volatile substances according to the present invention can also comprise a thermal cutoff component connected to the reflective element and a negative coefficient temperature element in contact with the reflective element, for measuring the temperature of the reflective element and modifying the power supply to the device by an electronic circuit according to the measured temperature.

Preferably, the device for evaporating volatile substances according to the present invention also comprises a cover for covering the wick, the heating element and the reflective element.

An advantage of the device according to the present invention is to have a very low thermal inertia. In comparison to a standard heater made with a rod-like resistor (such as metal oxide), that needs 15 to 20 min to reach working temperature, the device of the invention can reach the working temperature in seconds, such a 10-20 seconds.

BRIEF DESCRIPTION OF THE DRAWINGS

For a better comprehension of what has been disclosed, some drawings are attached in which, diagrammatically and only as a non-limitative example, a practical embodiment is shown.

DETAILED DESCRIPTION

Figure 1:
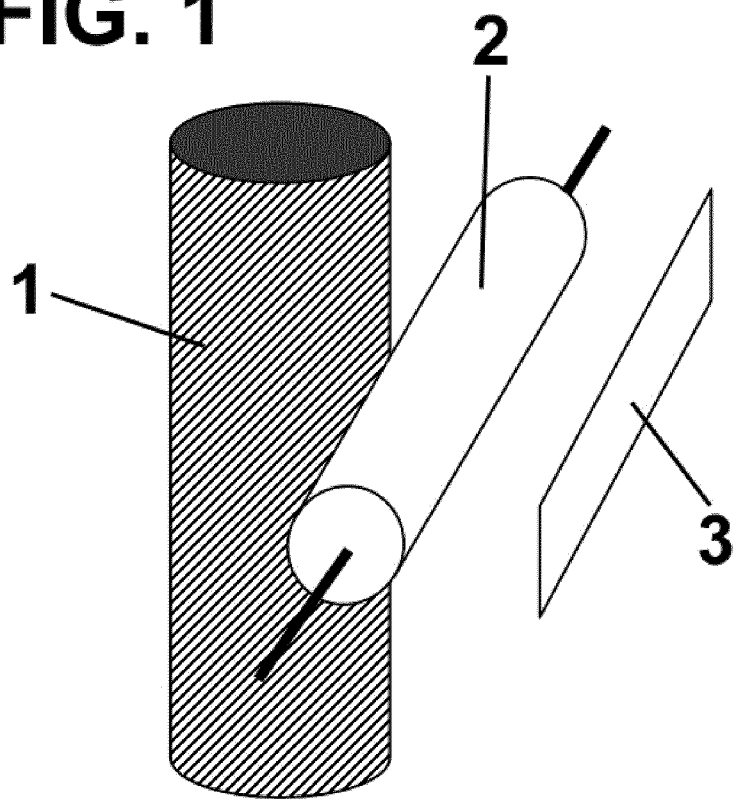
FIG. 1 is a diagrammatical perspective view of the device for evaporating volatile substances of the present invention, according to a first embodiment.

The device for evaporating volatile substances comprises a wick 1 impregnated with volatile substances and a heating element 2 that heats the wick 1 for evaporating said volatile substances. The device also comprises a reflective element 3 for reflecting the heat from the heating element 2 to said wick 1.

It must be pointed out that in the drawings is only shown a portion of the device for simplicity reasons, because the rest of the device is conventional and obvious for a person skilled in the art.

In FIG. 1 a first embodiment of the device according to the present invention is shown.

In this first embodiment, the heating element 2 is a standard rod shape resistor (such as a metal oxide resistor) and the reflective element 3 is a metallic wall placed on the opposite position regarding the wick.

Figure 2:
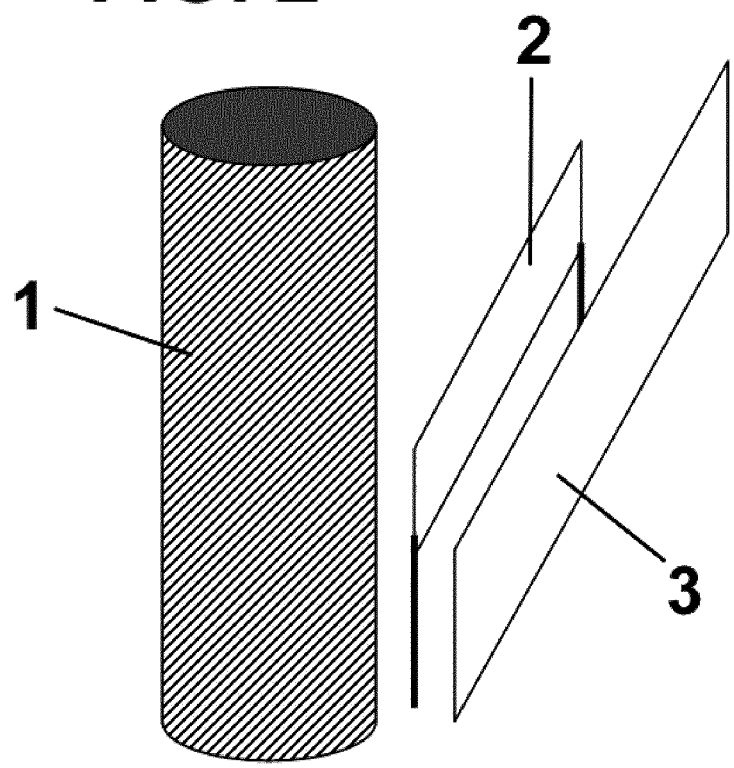
FIG. 2 is a diagrammatical perspective view of the device for evaporating volatile substances of the present invention, according to a second embodiment.

In an alternative embodiment, shown in FIG. 2, the geometry of the heating element can be changed. In this embodiment, the heating element 2 has a flat geometry and the reflective element 3 is a metallic wall with a mirror polish finishing. In this case, the heating element 2 is a metal ceramic heater with a thickness e.g. from 1 to 2 mm. This kind of heater has very low thermal inertia and can be heated very fast up to the targeted working temperature.

Figure 3:
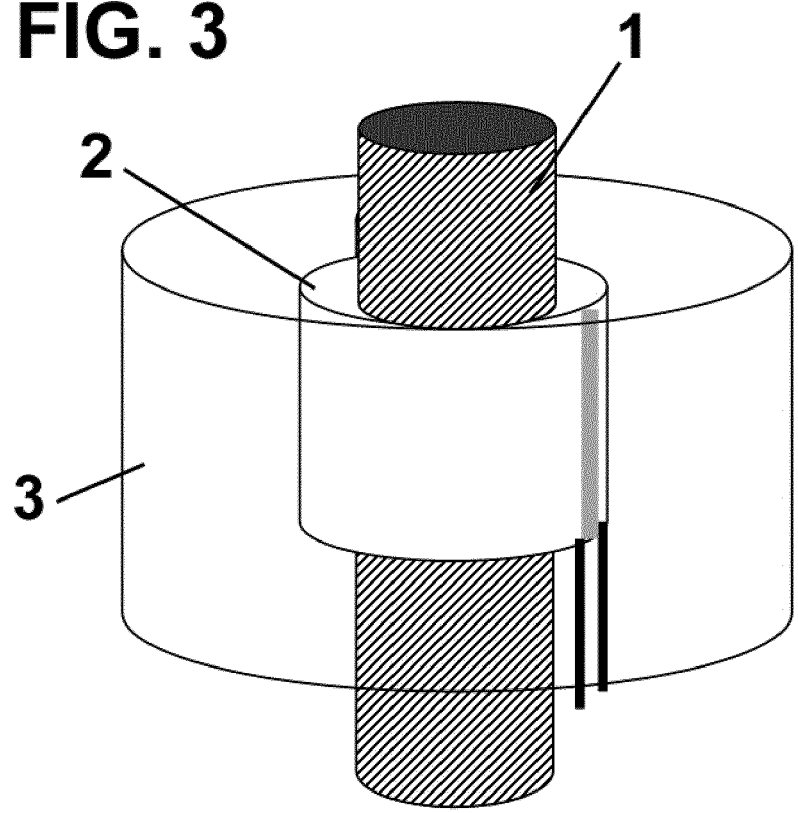
FIG. 3 is a diagrammatical perspective view of the device for evaporating volatile substances of the present invention, according to a third embodiment.

In a further alternative embodiment, shown in FIG. 3, the geometry of both the heating element 2 and reflective element 3 is similar to the geometry of the wick 1. With the wick 1 being a standard cylindrical wick, the heater has a tubular or cylindrical shape, preferably done by a metal ceramic heater. The reflective element 3 also has a tubular or cylindrical geometry.

Figure 4:
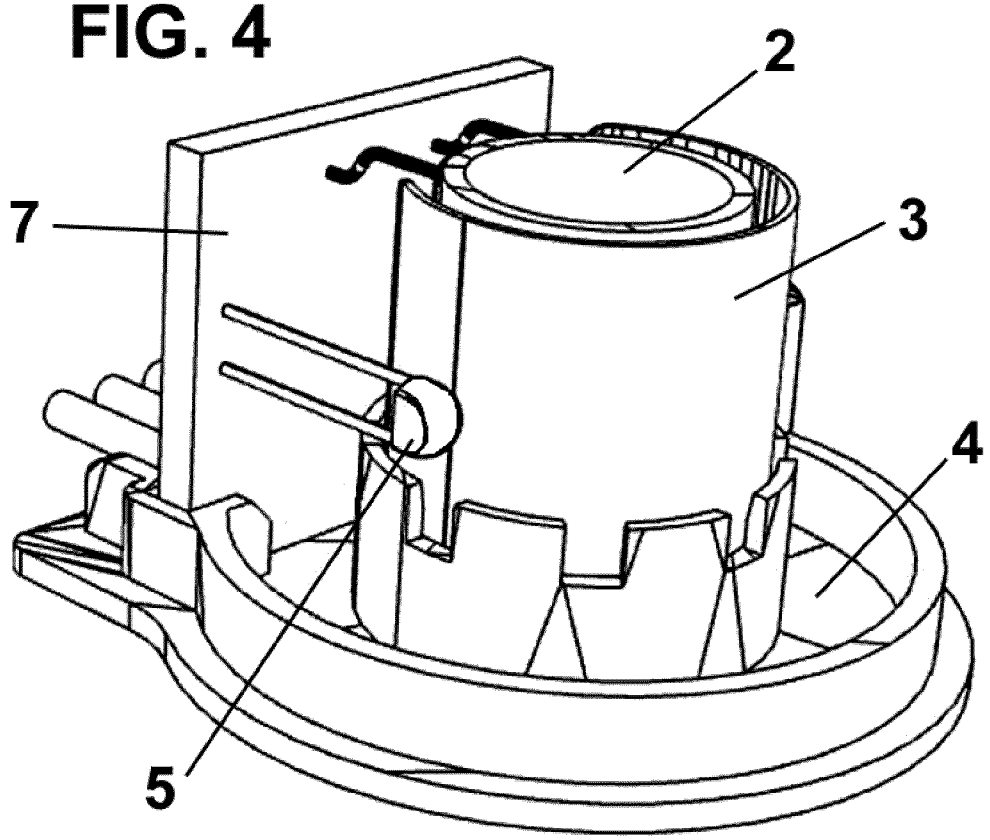
FIG. 4 is a diagrammatical perspective view of the device for evaporating volatile substances of the present invention, according to a fourth embodiment.

In an alternative embodiment shown in FIG. 4 the wick 1 is not shown, because it is placed inside the cylinder defined by the heating element 2. In this case, the diameter of the wick 1 can be in the range of 4-5 mm, and the heating element can be a metal ceramic heater with a thickness of 2 mm, an internal diameter of 9 mm and a height of 12 mm.

Regarding the reflective element 3, a preferred option is a metallic element with a thickness of 1 mm and a light reflectance higher than 30% over the light spectrum from over 400 nm, including the infrared spectrum. However, any kind of reflective element 3 suitable for reflecting the heat to the wick 1 can be used.

One preferred material for this reflective surface is aluminum, but alternative materials like silver, copper, gold or the like can also be used.

Furthermore, even having a lower performance and lower reflectance, alternative materials could be considered, such as e.g. plastic material having improved thermal conductive properties by adding boron or carbon nitride, or with filler, like talcum or glass fibre, or polymers. The use of this kind of material permits easier manufacturing (also in terms of costs), but provides a lower performance that a metallic reflective element.

As an alternative, the reflective element 3 can made from two layers: one having a high reflectivity and placed on the inner side of the cylinder and another layer having low thermal conductivity and placed on the outer side of the cylinder.

This construction with two layers can be done simply putting two separate layers in contact and mechanically maintaining them together by a plastic base 4 of the device. Alternatively, the two layers could be joined together by any conventional known means.

Also alternatively, the high reflective layer can be made by deposition of a metallic thin film layer on the inner side of a low thermal conductivity material.

As an additional improvement, a thermal cutoff component 5 can be connected to the reflective element 3. The function of this thermal cutoff element 5 is to guarantee the safety of the device, interrupting the power supply in case that an abnormal high temperature is measured.

In another additional improvement, a negative coefficient temperature element can be connected to the external surface of the reflective element 3. This negative coefficient temperature element is not shown in the drawings, but it can be placed at the other side opposite to the thermal cutoff component 5, and it can be used in addition or in place to this thermal cutoff component 5.

The function of this negative coefficient temperature element is to measure the temperature of the reflective element 3 and, in connection with an electronic circuit, to modify the power supply in order to adapt the wick temperature to compensate possible variations of voltage. These variations of voltage could be due to frequently detected voltage variation in the domestic plugs (more critical in an emerging country) or also progressive decay of voltage in a device supplied by batteries.

As shown in FIG. 4, and being also applicable to the other embodiments, the device preferably comprises a base 4, preferably made from plastic material, for the assembly of the components of the device. Furthermore, the device according to the present invention can also comprise a printed circuit board 7 as electronic control means for controlling the operation of the device.

E.g. this electronic control means can control the operation of the device providing peaks of higher intensity and period of lower intensity and in such a way to fight against well known phenomenon of olfactive habituation.

In a preferred embodiment, the device also includes a cover or housing, not shown in the drawings, which is provided with a plug to be connected to the mains.

One of the advantage of this construction, especially when using a MCH heater is to have a very low thermal inertia. Regarding standard heater made with a rod-like resistor (such as metal oxide), that typically needs 15 to 20 min to reach working temperature, the heater of the invention can reach working temperature in seconds, such a 10-20 s.

Even though reference is made to a specific embodiment of the invention, it is clear for a person skilled in the art that the disclosed device is susceptible of variations and modifications, and that all the details cited can be substituted by other technically equivalent ones, without departing from the scope of protection defined by the attached claims.

The invention claimed is:

1. A heating component for placement inside the housing of a device for evaporating volatile substances, the heating component comprising:
   a cylindrical heating element having a core sized and shaped to receive a wick impregnated with a volatile substance and that heats the wick for evaporating said volatile substances;
   a cylindrical reflective element for reflecting the heat from the heating element to the wick; and
   wherein when the heating element receives the wick, the heating element is located between the wick and the reflective element.

2. The heating component according to claim 1, wherein the heating element is a resistor or a ceramic heater.

3. The heating component according to claim 1 wherein the reflective element comprises a metallic surface.

4. The heating component according to claim 1 wherein said heating element and said reflective element are joined by a base.

5. The heating component according to claim 1 wherein said reflective element is made from two layers, a reflective layer and a base layer.

6. The heating component according to claim 1 further comprising a thermal cutoff component connected to the reflective element.

7. The heating component according to claim 1 further comprising a negative coefficient temperature element in contact with the reflective element for measuring the temperature of the reflective element and modifying a power supply to the device by an electronic circuit according to the measured temperature.

8. The heating component according to claim 2, wherein the reflective element comprises a metallic surface.

\* \* \* \* \*